US006306827B1

(12) United States Patent
Kinosaki et al.

(10) Patent No.: US 6,306,827 B1
(45) Date of Patent: Oct. 23, 2001

(54) METHOD FOR PREVENTING AND/OR TREATING RENAL DISEASE (75) Inventors: Masahiko Kinosaki; Hiromi Ogawa; Hiroaki Masunaga; Fumie Kobayashi, all of Tochigi; Kyoji Yamaguchi; Kanji Higashio, both of Saitama, all of (JP)

(73) Assignee: Snow Brand Milk Products Co., Ltd., Hokkaido (JP)

( * ) Notice: Subject to any disclaimer, the term of this patent is extended or adjusted under 35 U.S.C. 154(b) by 0 days.

(21) Appl. No.: 09/194,326

(22) PCT Filed: Mar. 20, 1998

(86) PCT No.: PCT/JP98/01221

§ 371 Date: Nov. 24, 1998

§ 102(e) Date: Nov. 24, 1998

(87) PCT Pub. No.: WO98/43665

PCT Pub. Date: Oct. 8, 1998

(30) Foreign Application Priority Data

Mar. 28, 1997 (JP) .................................................. 9-094989

(51) Int. Cl.⁷ .................................................. A61K 38/16
(52) U.S. Cl. ................................. 514/12; 514/2; 530/350; 530/395; 435/69.1; 435/69.4
(58) Field of Search .......................... 514/2, 12; 530/350, 530/335; 435/69.1, 69.4

(56) References Cited

FOREIGN PATENT DOCUMENTS

| 0 588 477 | 3/1994 | (EP) . |
| 0 757 994 | 2/1997 | (EP) . |
| 64-68400 | 3/1989 | (JP) . |
| 6-40935 | 2/1994 | (JP) . |
| WO96/202214 | 7/1996 | (WO) . |

OTHER PUBLICATIONS

Goodman & Gilman Teh Pharmacological Basis of Therapeutics. 9th Edition, p.1654–59.*

Toyohiro Takehara et al., "Structure of Hapatic Cell Growth Factor (HGF) and Physiological Effect" *Protein, Nucleic Acid and Enzyne*, vol. 36, No. 7, 1991, pp. 265–274.

Nobuyuki Shima et al., "Structure of Tumor Cell Damage Factor (F–TCF) and Various Bioactivity" *The Japanese Journal of Clinical Medicine*, vol. 50, No. 8, 1992, pp. 270–274.

International Search Report for PCT/JP98/01221.

* cited by examiner

*Primary Examiner*—Michael Borin
(74) *Attorney, Agent, or Firm*—Testa, Hurwitz & Thibeault, LLP (57) ABSTRACT A preventative and/or therapeutic agent to treat and/or prevent organ failure due to mercury exposure, contains as the active ingredient a mutant tumor cytotoxic factor protein (TCF-II). The therapeutic agent comprises a mutant TCF-II protein according to SEQ ID NO. 2 in which amino acid residues Arg-Lys-Arg-Arg have been replaced by Ala-Ala-Ala-Ala, or in which amino acids Lys-Ile-Lys-Thr-Lys-Lys have been replaced by Ala-Ile-Ala-Thr-Ala-Ala (SEQ ID NO. 3).

5 Claims, 2 Drawing Sheets

METHOD FOR PREVENTING AND/OR TREATING RENAL DISEASE

RELATED APPLICATIONS

This application is a filing under 35 USC §371 of international application number PCT/JP98/01221, filed Mar. 20, 1998, which claims priority to Japanese patent application number 9/94989, filed Mar. 28, 1997.

TECHNOLOGICAL FIELD

The present invention relates to an agent for preventing and/or treating renal disease comprising point mutant TCF-II mutant as an effective ingredient. The agent for preventing and/or treating renal disease of the present invention is useful for preventing and/or treating renal diseases such as chronic nephropathy related with ischemic renal disorder, drug-induced renal disorder, diabetic nephropathy, glomerular nephropathy, glomerulosclerosis, membranous nephropathy, autoimmune disease and nephrose or renal insufficiency caused by the above.

BACKGROUND TECHNOLOGY

Any effective therapeutic agent for renal diseases such as chronic nephropathy related with ischemic renal disorder, drug-induced renal disorder, diabetic nephropathy, glomerular nephropathy, glomerulosclerosis, membranous nephropathy, autoimmune disease and nephrose or renal insufficiency caused by the above has not been found so far. In a clinical practice, only maintenance therapy, that is, removal of derangement by dialysis, management of nutrition or administration of diuretic or cardiac or steroid therapy is carried out considering symptoms. Therefore, an effective drug in renal diseases is eagerly desired.

TCF-II (SEQ ID NO:1) is a glycoprotein(WO 90/10651) found by the present inventors which is known as Tumor Necrosis Factor produced by human fibroblast IMR-90 and has excellent pharmacological activities such as an activity of proliferating hepatocyte, an activity of proliferating renal cell, an anti-tumor activity and so on. Naturally occurring TCF-II and recombinant TCF-II are known. Further, a mutant protein without carbohydrate chain and a point mutant TCF-II (WO 96/20214) are also known.

DISCLOSURE OF THE INVENTION

Considering the above situations, the present inventors eagerly investigated to look for an effective substance for these renal diseases and found that TCF-II mutant, especially, a TCF-II mutant which is a point mutant of amino acid sequence at the second from N-terminal, that is, from Arg-Lys-Arg-Arg to Ala-Ala-Ala-Ala or another TCF-II mutant whose amino acid sequence at 27 th from N-terminal was changed into Ala-Ile-Ala-Thr-Ala-Ala from Lys-Ile-Lys-Thr-Lys-Lys, was effective for preventing and/or treating renal diseases. Accordingly, an object of the present invention is to provide a novel agent for preventing and/or treating renal diseases comprising TCF-II mutant as an effective ingredient.

The present invention relates to an agent for preventing and/or treating renal diseases comprising TCF-II mutant, especially, a TCF-II mutant, such as the one disclosed in SEQ ID NO:2, which is a point mutant of amino acid sequence at the second from N-terminal, that is, from Arg-Lys-Arg-Arg to Ala-Ala-Ala-Ala or another TCF-II mutant such as the one disclosed in SEQ ID NO:3, whose amino acid sequence at 27 th from N-terminal was changed to Ala-Ile-Ala-Thr-Ala-Ala from Lys-Ile-Lys-Thr-Lys-Lys, as an effective ingredient. The agent for preventing and/or treating renal disease of the present invention is useful for preventing and/or treating renal diseases such as chronic nephropathy related with ischemic renal disorder, drug-induced renal disorder, diabetic nephropathy, glomerular nephropathy, glomerulosclerosis, membranous nephropathy, autoimmune disease and nephrose or renal insufficiency caused by the above.

Point mutant TCF-II of an effective ingredient of the present invention can be prepared by synthesizing oligonucleotide substituted with corresponding base sequence to mutation site of TCF-II mutant, followed by site-directed mutagenesis using TCF-II cDNA as a template by polymerase chain reaction (PCR) method. cDNA obtained as above can be inserted into a vector having an appropriate expression promoter (Cytomegalovirus (CMV), SRα (Mol. Cell. Biol. vol.8, No.1 pp466–472(1988)) and Japanese unexamined laid-open patent application No.277489 (1991)), followed by transfection thereof into eukariotic cell such as mammlian cell. TCF-II mutant desired can be prepared by recovering it from culture medium of the culture of the above transfected cell. As TCF-II mutant used in the present invention, any TCF-II with an artificial mutation can be used but, more preferably, a TCF-II mutant such as the one disclosed in SEQ ID NO:2, whose amino acid sequence at the second from N-terminal, was changed from Arg-Lys-Arg-Arg to Ala-Ala-Ala-Ala or another TCF-II mutant such as the one disclosed in SEQ ID NO:3, whose amino acid sequence at 27th from N-terminal was changed to Ala-Ile-Ala-Thr-Ala-Ala from Lys-Ile-Lys-Thr-Lys-Lys(these mutants were described in WO 96/20214) can be used.

The agent for preventing and/or treating renal diseases of the present invention can be administered intravenously, intra muscularly or subcutaneously as injections. This pharmaceutical preparation can be manufactured according to a known method of manufacturing pharmaceutical preparation and, if necessary, a pH conditioner, buffer, stabilizer etc. can be added thereto. Dose of the pharmaceutical preparation of the present invention can vary depending on degree of severeness of symptom, health conditions, age, body weight and will not be limited, but for an adult person per day pharmaceutical preparation containing 0.6 mg–600 mg of TCF-II, preferably 6 mg–60 mg, can be administered once or more per day.

BEST EMBODIMENT FOR PRACTICE OF THE INVENTION

The present invention will be described in more detail. However, these are only exemplification and will not limit the present invention.

EXAMPLE 1

Preparation of TCF-II Mutant

According to a method described in WO 96/20214, two species of point mutant,that is, a TCF-II mutant (SEQ ID NO: 2) whose amino acid sequence at the second from N-terminal was changed from Arg-Lys-Arg-Arg to Ala-Ala-Ala-Ala (hereinafter referred to RKRR2AkAA) and another TCF-II mutant (SEQ ID NO:3) whose amino acid sequence at 27th from N-terminal was changed from Lys-Ile-Lys-Thr-Lys-Lys to Ala-Ile-Ala-Thr-Ala-Ala (hereinafter referred to KIKTKK27AIATAA) were prepared. That is, shaking culture of *E. coli* comprising an expression vector of RKRR2AIAA cDNA (FERM BP-5266) and *E. coli* comprising an expression vector of KIKTKK27AIATAA cDNA was carried out in L-medium (400 ml) containing 50 μg/ml ampicillin at 37° C. When OD 600 became 1.0, spectinomycin (Sigma) was added so that the final concentration thereof would be 0.3 mg/ml, and the culture medium was cultured overnight. According to the method of Maniatis (Molecular Cloning 2nd ed. ppl.21–1. 52(1989), Cold Spring Harbor Laboratory), plasmid DNA was separated by alkaline SDS method and the expression plasmodia of each mutant was purified by cesium chloride density gradient centrifugation.

These obtained expression plasmodia (200 μg) were introduced into CHO cell. The expression plasmodia (200 μg) and expression plasmodia of pSV2 of blastsidine resistant gene (10 μg/Funakoshi) DNA which were dissolved in TE (10 mM Tris-HCl (pH 8.0)–1 mMEDTA) in advance, were transfected into $2 \times 10^6$ CHO cells suspended in 0.8 ml of IMDM culture medium (Gibco) containing 10% calf fetal serum by electroporation. After electroporation carried out under the conditions of 330 V and 960 μF, cell suspension was left at room temperature for 10 minutes, suspended in 10 ml IMDM culture medium containing 10% calf fetal serum and cultured in a $CO_2$ incubator (5% $CO_2$) at 37° C. for 2 days. After 2 days since then, cells were deprived from the bottom of flask by tripsin (Gibco) treatment and the number of viable cells was counted and cells were disseminated in 96-well plate (Nunc) so as to be 10,000 cells/well, which was cultured in 200 μl selected medium/well containing 5 μg/ml blastosidine (Funakoshi) at 37° C. in $CO_2$ incubator(5% $CO_2$). After 2–3 weeks, 50 μl of culture supernatant was taken from each well and, by enzyme-immuno-assay thereof (N.Shima et.al., Gastropenterologia Japonica, vol.26, No.4, pp 477–482 (1991)), cells producing TCF-II mutant were selected. TCF-II mutant producing cells were cultured in 50–200 flasks (each volume is 225 $cm^2$) containing 100 ml of culture medium at 37° C. in a $CO_2$ incubator (5% $CO_2$) for 4–7 days and 5–20 L of cultured supernatant was recovered. Each mutant was purified from the above culture supernatant using Heparin-Sepharose CL-6B column (25 mm×120 mm, Pharmacia), Mono S column (5 mm×50 mm, Pharmacia) and Heparin 5-PW column (8 mm×75 mm, Toso). Obtained TCF-II mutant was dialyzed against phosphate buffer solution (PBS) containing 0.01% Tween 20 to be the final product. The protein determination of the final product was carried out by lowery method and the purity thereof was examined by SDS electrophoresis and, then, amino acid sequencer thereof confirmed amino acid sequence.

EXAMPLE 2

Manufacturing of Pharmaceutical Preparation of TCF-II

An example of manufacturing injections of recombinant TCF-II obtained in example 1 was shown.

| (1) TCF-II Mutant | 20 μg |
|---|---|
| human serum albumin | 100 mg |

The above composition was dissolved in citric acid buffer solution with pH 6.03 so that the total volume would be 20ml. Then it was divided into vials containing 2 ml each after sterilization and sealed after lyophilization.

| (2) TCF-II Mutant | 20 μg |
|---|---|
| Tween 80 | 1 mg |
| human serum albumin | 100 mg |

The above composition was dissolved in physiological saline solution for injections so that the total volume would be 20 ml. Then it was divided into vials containing 2 ml each after sterilization and sealed after lyophilization.

| (3) TCF-II Mutant | 20 μg |
|---|---|
| Tween 80 | 2 mg |
| Sorbitol | 4 g |

The above composition was dissolved in citric acid buffer solution with pH 6.03 so that the total volume would be 20 ml. Then it was divided into vials containing 2 ml each after sterilization and sealed after lyophilization.

| (4) TCF-II Mutant | 20 μg |
|---|---|
| Tween 80 | 1 mg |
| Glycine | 2 g |

The above composition was dissolved in physiological saline solution foe injections so that the total volume would be 20 ml. Then it was divided into vials containing 2 ml each after sterilization and sealed after lyophilization.

| (5) TCF-II Mutant | 20 μg |
|---|---|
| Tween 80 | 1 mg |
| Sorbitol | 2 g |
| Glycine | 1 g |

The above composition was dissolved in physiological saline solution for injections so that the total volume would be 20 ml. Then it was divided into vials containing 2 ml each after sterilization and sealed after lyophilization.

| (6) TCF-II Mutant | 20 μg |
|---|---|
| Sorbitol | 4 g |
| human serum albumin | 50 mg |

The above composition was dissolved in citric acid buffer solution with pH 6.03 so that the total volume would be 20 ml. Then it was divided into vials containing 2 ml each after sterilization and sealed after lyophilization.

| (7) TCF-II Mutant | 20 µg |
|---|---|
| Glycine | 2 g |
| human serum albumin | 50 mg |

The above composition was dissolved in physiological saline solution for injections so that the total volume would be 20 ml. Then it was divided into vials containing 2 ml each after sterilization and sealed after lyophilization.

| (8) TCF-II Mutant | 20 µg |
|---|---|
| human serum albumin | 50 mg |

The above composition was dissolved in citric acid buffer solution with pH 6.03 so that the total volume would be 20 ml. Then it was divided into vials containing 2 ml each after sterilization and sealed after lyophilization.

These lyophilized products will be dissolved in sterilized distilled water on use.

Example 3

Defensive effect against death caused by renal insufficiency induced with mercuric chloride.

Defensive effect of TCF-II mutant against death caused by renal insufficiency induced with mercuric chloride was examined using RKRR2AAAA mutated at the second amino acid from N-terminal of TCF-II RKRR2AAAA in which the amino acid residues from the N-terminal of TCF-II and KIKTKK27AIATAA in which the amino acid residues from the 27th amino acid, which were obtained in example 1.

Figure 1:
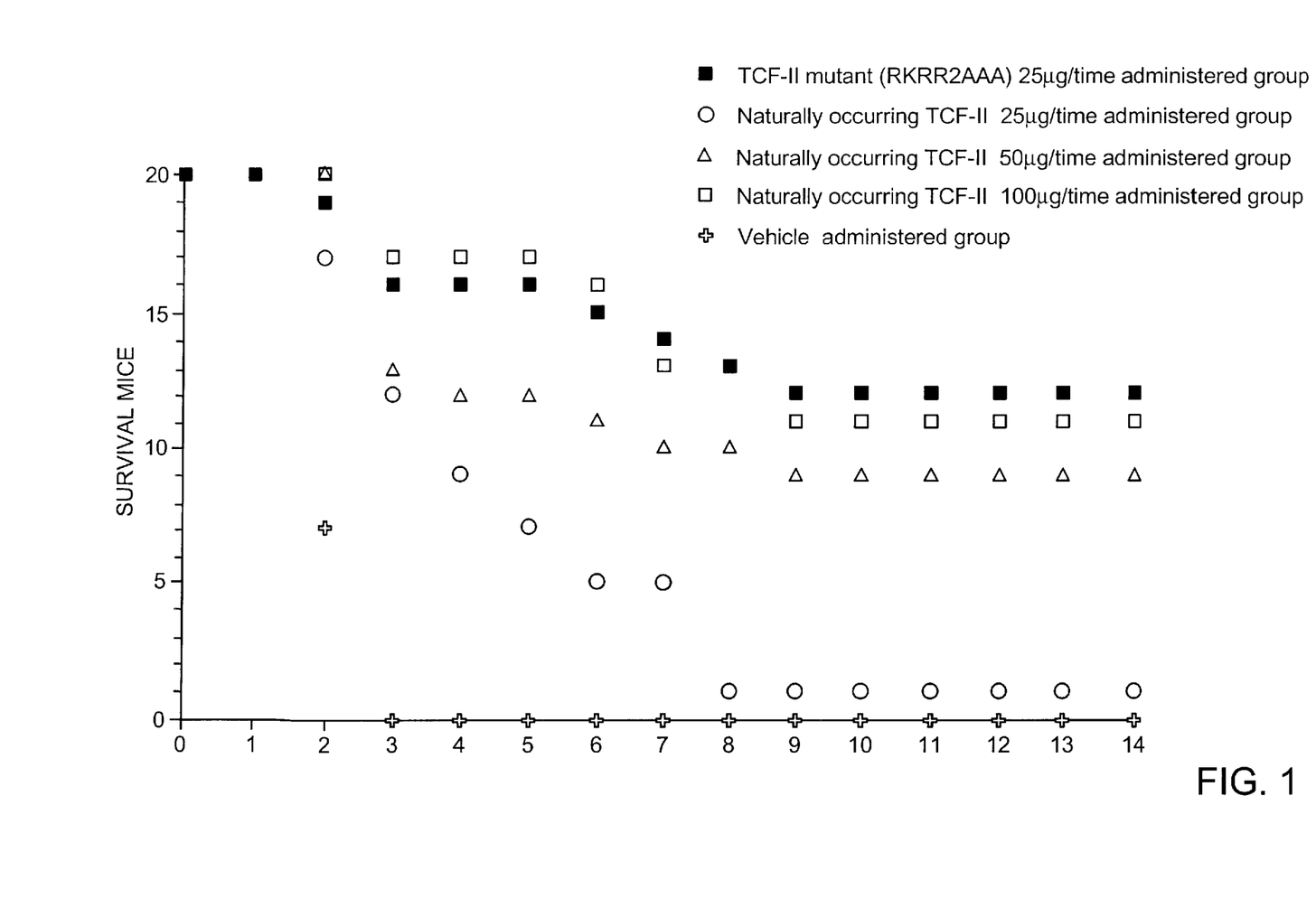
FIG. 1 shows defensive effect of TCF-II mutant (RKRR2AAAA) against death caused by renal insufficiency induced with mercuric chloride in example 3.
Figure 2:
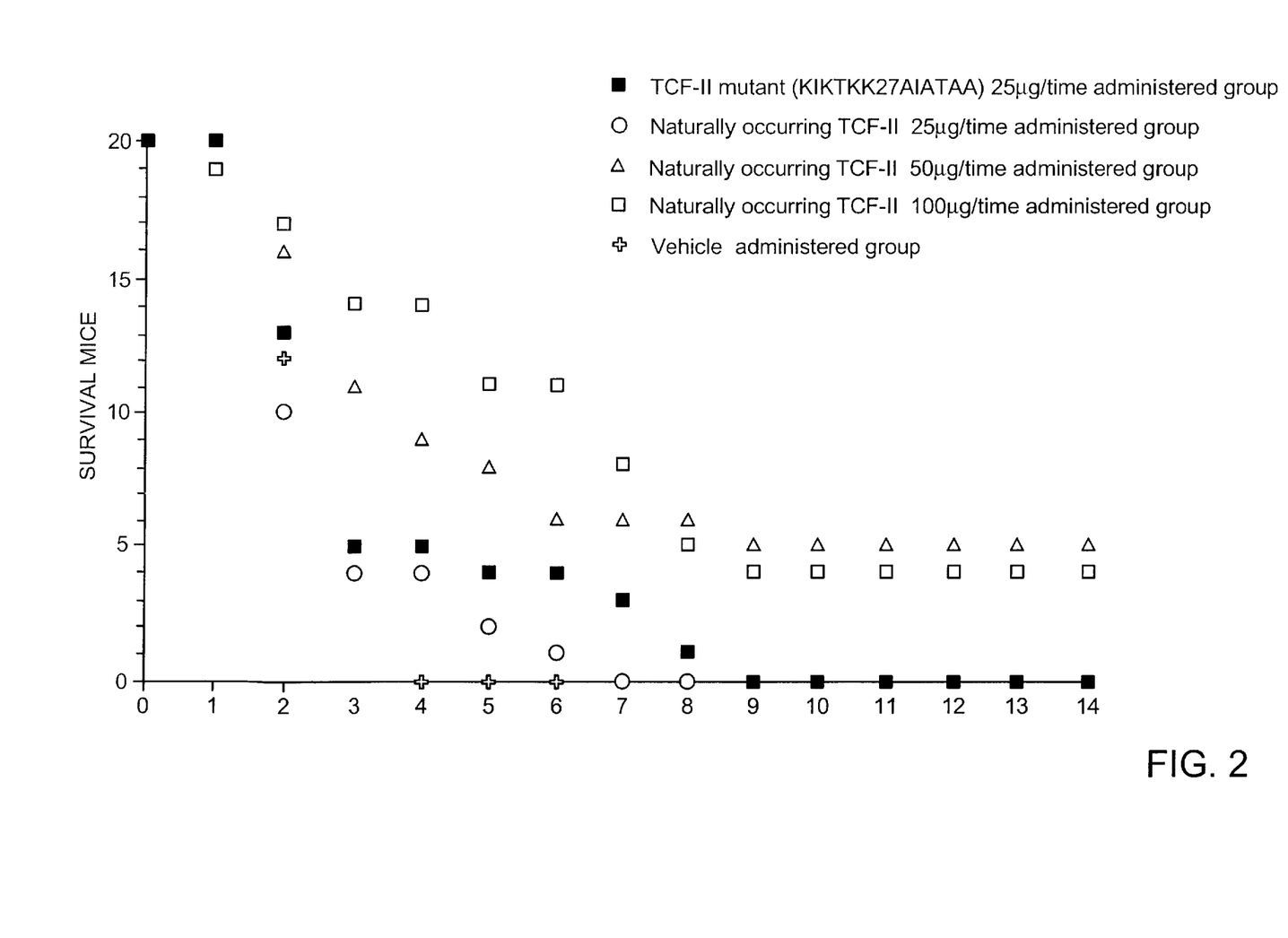
FIG. 2 shows defensive effect of TCF-II mutant (KIKTKK27AIATAA) against death caused by renal insufficiency induced with mercuric chloride in example 3.

That is, one of TCF-II mutants (25 µg/mouse/time), TCF-II as positive control (25, 50, 100 µg/mouse/time), or vehicle was administered intravenously to male ICR mice (body weight:30–35 g; n=20 per group) twice daily (total 9 times). At 6 hours after the final administration, 5 mg/kg mercuric chloride (Wako-junyaku) was administered intravenously, and the survival of mice was monitored to examine the protective effect of TCF-II mutant on mortality. The results are shown in FIG. 1 and FIG. 2. From the results, the TCF-II treatment and TCF-II mutant treatment apparently protected the mortality caused by mercuric chloride—induced renal failure, compared to the vehicle treatment. Furthermore, the activities of TCF-II mutants were more potent than that of TCF-II (RKRR2AAAA was four times and KIKTKK27AIATAA was two times as potent as native TCF-II).

INDUSTRIAL APPLICABILITY

The present invention provides an agent for preventing and/or treating renal diseases.

The present invention is useful for preventing and/or treating renal diseases such as chronic nephropathy related with ischemic renal disorder, drug-induced renal disorder, diabetic nephropathy, glomerular nephropathy, glomerulosclerosis, membranous nephropathy, autoimmune disease and nephrose or renal insufficiency caused by the above, comprising TCF-II mutants, that is, a TCF-II mutant, such as the one disclosed in SEQ ID NO:2, in which amino acid sequence at the second from N-terminal of TCF-II was changed from Arg-Lys-Arg-Arg to Ala-Ala-Ala-Ala and another TCF-II mutant, such as the one disclosed in SEQ ID NO:3, in which amino acid sequence at the 27th from the N-terminus was changed from Lys-Ile-Lys-Thr-Lys-Lys to Ala-Ile-Ala-Thr-Ala-Ala as an effective ingredient.

Reference of Microorganism

1) Organization of Deposition

National Institute of Bioscience and Human-Technology,
Agency of Industrial Science and Technology,
Ministry of International Trade and Industry
Address: 1–3, Higashi 1-chome, Tsukuba-shi, Ibaraki-ken, Japan
Date of Deposition: Nov. 10, 1994
(The microorganism was originally deposited above of Nov. 10, 1994, and transferred to the deposit based on the Treaty on Oct. 25, 1995)
Accession Number: FERM BP-5265

2) Organization of Deposition

National Institute of Bioscience and Human-Technology,
Agency of Industrial Science and Technology,
Ministry of International Trade and Industry
Address: 1–3, Higashi 1-chome, Tsukuba-shi, Ibaraki-ken, Japan
Date of Deposition: Nov. 10, 1994
(The microorganism was originally deposited above of Nov. 10, 1994, and transferred to the deposit based on the Treaty on Oct. 25, 1995)
Accession Number: FERM BP-5266

What is claimed is:

1. A method of treating renal failure due to mercury exposure, comprising:
   administering to a patient who has been exposed to mercury, an effective amount of a pharmaceutical preparation comprising a mutant TCF-II protein according to SEQ ID NO. 2 in which amino acid residues Arg-Lys-Arg-Arg have been replaced by Ala-Ala-Ala-Ala, or a pharmacologically acceptable salt thereof.

2. A method of treating renal failure due to mercury exposure, comprising:
   administering to a patient who has been exposed to mercury, an effective amount of a pharmaceutical preparation comprising a mutant TCF-II protein according to SEQ ID NO. 3 in which amino acid residues Lys-Ile-Lys-Thre-Lys-Lys have been replaced by Ala-Ile-Ala-Thre-Ala-Ala, or a pharmaceutical salt thereof.

3. The method of claim 1 or 2, in which the mutant TCF-II protein is a recombinant TCF II protein.

4. The method of claim 1 or 3 wherein the pharmaceutical preparation comprises 0.6 mg–600 mg of the mutant TCF-II.

5. The method of claim 4. wherein the pharmaceutical preparation comprises 6 mg–60 mg of the mutant TCF II.

* * * * *

SEQUENCE LISTING

<160> NUMBER OF SEQ ID NOS: 3

<210> SEQ ID NO 1
<211> LENGTH: 723
<212> TYPE: PRT
<213> ORGANISM: Homo sapiens
<220> FEATURE:
<223> OTHER INFORMATION: TCF-II

<400> SEQUENCE: 1

Met Trp Val Thr Lys Leu Leu Pro Ala Leu Leu Leu Gln His Val Leu
-31 -30                  -25                  -20

Leu His Leu Leu Leu Leu Pro Ile Ala Ile Pro Tyr Ala Glu Gly Gln
-15                  -10                  -5              -1   1

-continued

```
Arg Lys Arg Arg Asn Thr Ile His Glu Phe Lys Lys Ser Ala Lys Thr
                5                  10                 15
Thr Leu Ile Lys Ile Asp Pro Ala Leu Lys Ile Lys Thr Lys Lys Val
             20                 25                 30
Asn Thr Ala Asp Gln Cys Ala Asn Arg Cys Thr Arg Asn Lys Gly Leu
         35                 40                 45
Pro Phe Thr Cys Lys Ala Phe Val Phe Asp Lys Ala Arg Lys Gln Cys
 50                 55                 60                 65
Leu Trp Phe Pro Phe Asn Ser Met Ser Ser Gly Val Lys Lys Glu Phe
                70                 75                 80
Gly His Glu Phe Asp Leu Tyr Glu Asn Lys Asp Tyr Ile Arg Asn Cys
             85                 90                 95
Ile Ile Gly Lys Gly Arg Ser Tyr Lys Gly Thr Val Ser Ile Thr Lys
         100                105                110
Ser Gly Ile Lys Cys Gln Pro Trp Ser Ser Met Ile Pro His Glu His
115                120                125
Ser Tyr Arg Gly Lys Asp Leu Gln Glu Asn Tyr Cys Arg Asn Pro Arg
130                135                140                145
Gly Glu Glu Gly Gly Pro Trp Cys Phe Thr Ser Asn Pro Glu Val Arg
                150                155                160
Tyr Glu Val Cys Asp Ile Pro Gln Cys Ser Glu Val Glu Cys Met Thr
             165                170                175
Cys Asn Gly Glu Ser Tyr Arg Gly Leu Met Asp His Thr Glu Ser Gly
         180                185                190
Lys Ile Cys Gln Arg Trp Asp His Gln Thr Pro His Arg His Lys Phe
195                200                205
Leu Pro Glu Arg Tyr Pro Asp Lys Gly Phe Asp Asp Asn Tyr Cys Arg
210                215                220                225
Asn Pro Asp Gly Gln Pro Arg Pro Trp Cys Tyr Thr Leu Asp Pro His
                230                235                240
Thr Arg Trp Glu Tyr Cys Ala Ile Lys Thr Cys Ala Asp Asn Thr Met
             245                250                255
Asn Asp Thr Asp Val Pro Leu Glu Thr Thr Glu Cys Ile Gln Gly Gln
         260                265                270
Gly Glu Gly Tyr Arg Gly Thr Val Asn Thr Ile Trp Asn Gly Ile Pro
275                280                285
Cys Gln Arg Trp Asp Ser Gln Tyr Pro His Glu His Asp Met Thr Pro
290                295                300                305
Glu Asn Phe Lys Cys Lys Asp Leu Arg Glu Asn Tyr Cys Arg Asn Pro
                310                315                320
Asp Gly Ser Glu Ser Pro Trp Cys Phe Thr Thr Asp Pro Asn Ile Arg
             325                330                335
Val Gly Tyr Cys Ser Gln Ile Pro Asn Cys Asp Met Ser His Gly Gln
         340                345                350
Asp Cys Tyr Arg Gly Asn Gly Lys Asn Tyr Met Gly Asn Leu Ser Gln
355                360                365
Thr Arg Ser Gly Leu Thr Cys Ser Met Trp Asp Lys Asn Met Glu Asp
370                375                380                385
Leu His Arg His Ile Phe Trp Glu Pro Asp Ala Ser Lys Leu Asn Glu
                390                395                400
Asn Tyr Cys Arg Asn Pro Asp Asp Asp Ala His Gly Pro Trp Cys Tyr
             405                410                415
```

```
Thr Gly Asn Pro Leu Ile Pro Trp Asp Tyr Cys Pro Ile Ser Arg Cys
            420                 425                 430

Glu Gly Asp Thr Thr Pro Thr Ile Val Asn Leu Asp His Pro Val Ile
            435                 440                 445

Ser Cys Ala Lys Thr Lys Gln Leu Arg Val Val Asn Gly Ile Pro Thr
450                 455                 460                 465

Arg Thr Asn Ile Gly Trp Met Val Ser Leu Arg Tyr Arg Asn Lys His
                470                 475                 480

Ile Cys Gly Gly Ser Leu Ile Lys Glu Ser Trp Val Leu Thr Ala Arg
            485                 490                 495

Gln Cys Phe Pro Ser Arg Asp Leu Lys Asp Tyr Glu Ala Trp Leu Gly
            500                 505                 510

Ile His Asp Val His Gly Arg Gly Asp Glu Lys Cys Lys Gln Val Leu
            515                 520                 525

Asn Val Ser Gln Leu Val Tyr Gly Pro Glu Gly Ser Asp Leu Val Leu
530                 535                 540                 545

Met Lys Leu Ala Arg Pro Ala Val Leu Asp Asp Phe Val Ser Thr Ile
                550                 555                 560

Asp Leu Pro Asn Tyr Gly Cys Thr Ile Pro Glu Lys Thr Ser Cys Ser
            565                 570                 575

Val Tyr Gly Trp Gly Tyr Thr Gly Leu Ile Asn Tyr Asp Gly Leu Leu
            580                 585                 590

Arg Val Ala His Leu Tyr Ile Met Gly Asn Glu Lys Cys Ser Gln His
595                 600                 605

His Arg Gly Lys Val Thr Leu Asn Glu Ser Glu Ile Cys Ala Gly Ala
610                 615                 620                 625

Glu Lys Ile Gly Ser Gly Pro Cys Glu Gly Asp Tyr Gly Gly Pro Leu
                630                 635                 640

Val Cys Glu Gln His Lys Met Arg Met Val Leu Gly Val Ile Val Pro
            645                 650                 655

Gly Arg Gly Cys Ala Ile Pro Asn Arg Pro Gly Ile Phe Val Arg Val
            660                 665                 670

Ala Tyr Tyr Ala Lys Trp Ile His Lys Ile Ile Leu Thr Tyr Lys Val
675                 680                 685

Pro Gln Ser
690

<210> SEQ ID NO 2
<211> LENGTH: 723
<212> TYPE: PRT
<213> ORGANISM: Artificial Sequence
<220> FEATURE:
<223> OTHER INFORMATION: Description of Artificial Sequence:RKRR2AAAA
      mutant of TCF-II

<400> SEQUENCE: 2

Met Trp Val Thr Lys Leu Leu Pro Ala Leu Leu Leu Gln His Val Leu
-31 -30             -25                 -20

Leu His Leu Leu Leu Leu Pro Ile Ala Ile Pro Tyr Ala Glu Gly Gln
-15                 -10                 -5                  -1   1

Ala Ala Ala Ala Asn Thr Ile His Glu Phe Lys Lys Ser Ala Lys Thr
                5                   10                  15

Thr Leu Ile Lys Ile Asp Pro Ala Leu Lys Ile Lys Thr Lys Lys Val
            20                  25                  30

Asn Thr Ala Asp Gln Cys Ala Asn Arg Cys Thr Arg Asn Lys Gly Leu
            35                  40                  45
```

```
Pro Phe Thr Cys Lys Ala Phe Val Phe Asp Lys Ala Arg Lys Gln Cys
 50                  55                  60                  65

Leu Trp Phe Pro Phe Asn Ser Met Ser Ser Gly Val Lys Lys Glu Phe
                 70                  75                  80

Gly His Glu Phe Asp Leu Tyr Glu Asn Lys Asp Tyr Ile Arg Asn Cys
                 85                  90                  95

Ile Ile Gly Lys Gly Arg Ser Tyr Lys Gly Thr Val Ser Ile Thr Lys
            100                 105                 110

Ser Gly Ile Lys Cys Gln Pro Trp Ser Ser Met Ile Pro His Glu His
115                 120                 125

Ser Tyr Arg Gly Lys Asp Leu Gln Glu Asn Tyr Cys Arg Asn Pro Arg
130                 135                 140                 145

Gly Glu Glu Gly Gly Pro Trp Cys Phe Thr Ser Asn Pro Glu Val Arg
                150                 155                 160

Tyr Glu Val Cys Asp Ile Pro Gln Cys Ser Glu Val Glu Cys Met Thr
            165                 170                 175

Cys Asn Gly Glu Ser Tyr Arg Gly Leu Met Asp His Thr Glu Ser Gly
            180                 185                 190

Lys Ile Cys Gln Arg Trp Asp His Gln Thr Pro His Arg His Lys Phe
195                 200                 205

Leu Pro Glu Arg Tyr Pro Asp Lys Gly Phe Asp Asp Asn Tyr Cys Arg
210                 215                 220                 225

Asn Pro Asp Gly Gln Pro Arg Pro Trp Cys Tyr Thr Leu Asp Pro His
                230                 235                 240

Thr Arg Trp Glu Tyr Cys Ala Ile Lys Thr Cys Ala Asp Asn Thr Met
            245                 250                 255

Asn Asp Thr Asp Val Pro Leu Glu Thr Thr Glu Cys Ile Gln Gly Gln
            260                 265                 270

Gly Glu Gly Tyr Arg Gly Thr Val Asn Thr Ile Trp Asn Gly Ile Pro
275                 280                 285

Cys Gln Arg Trp Asp Ser Gln Tyr Pro His Glu His Asp Met Thr Pro
290                 295                 300                 305

Glu Asn Phe Lys Cys Lys Asp Leu Arg Glu Asn Tyr Cys Arg Asn Pro
                310                 315                 320

Asp Gly Ser Glu Ser Pro Trp Cys Phe Thr Thr Asp Pro Asn Ile Arg
            325                 330                 335

Val Gly Tyr Cys Ser Gln Ile Pro Asn Cys Asp Met Ser His Gly Gln
            340                 345                 350

Asp Cys Tyr Arg Gly Asn Gly Lys Asn Tyr Met Gly Asn Leu Ser Gln
355                 360                 365

Thr Arg Ser Gly Leu Thr Cys Ser Met Trp Asp Lys Asn Met Glu Asp
370                 375                 380                 385

Leu His Arg His Ile Phe Trp Glu Pro Asp Ala Ser Lys Leu Asn Glu
                390                 395                 400

Asn Tyr Cys Arg Asn Pro Asp Asp Asp Ala His Gly Pro Trp Cys Tyr
            405                 410                 415

Thr Gly Asn Pro Leu Ile Pro Trp Asp Tyr Cys Pro Ile Ser Arg Cys
            420                 425                 430

Glu Gly Asp Thr Thr Pro Thr Ile Val Asn Leu Asp His Pro Val Ile
            435                 440                 445

Ser Cys Ala Lys Thr Lys Gln Leu Arg Val Val Asn Gly Ile Pro Thr
450                 455                 460                 465
```

-continued

```
Arg Thr Asn Ile Gly Trp Met Val Ser Leu Arg Tyr Arg Asn Lys His
                470                 475                 480

Ile Cys Gly Gly Ser Leu Ile Lys Glu Ser Trp Val Leu Thr Ala Arg
            485                 490                 495

Gln Cys Phe Pro Ser Arg Asp Leu Lys Asp Tyr Glu Ala Trp Leu Gly
        500                 505                 510

Ile His Asp Val His Gly Arg Gly Asp Glu Lys Cys Lys Gln Val Leu
    515                 520                 525

Asn Val Ser Gln Leu Val Tyr Gly Pro Glu Gly Ser Asp Leu Val Leu
530                 535                 540                 545

Met Lys Leu Ala Arg Pro Ala Val Leu Asp Asp Phe Val Ser Thr Ile
                550                 555                 560

Asp Leu Pro Asn Tyr Gly Cys Thr Ile Pro Glu Lys Thr Ser Cys Ser
            565                 570                 575

Val Tyr Gly Trp Gly Tyr Thr Gly Leu Ile Asn Tyr Asp Gly Leu Leu
        580                 585                 590

Arg Val Ala His Leu Tyr Ile Met Gly Asn Glu Lys Cys Ser Gln His
    595                 600                 605

His Arg Gly Lys Val Thr Leu Asn Glu Ser Glu Ile Cys Ala Gly Ala
610                 615                 620                 625

Glu Lys Ile Gly Ser Gly Pro Cys Glu Gly Asp Tyr Gly Gly Pro Leu
                630                 635                 640

Val Cys Glu Gln His Lys Met Arg Met Val Leu Gly Val Ile Val Pro
            645                 650                 655

Gly Arg Gly Cys Ala Ile Pro Asn Arg Pro Gly Ile Phe Val Arg Val
        660                 665                 670

Ala Tyr Tyr Ala Lys Trp Ile His Lys Ile Ile Leu Thr Tyr Lys Val
    675                 680                 685

Pro Gln Ser
690
```

<210> SEQ ID NO 3
<211> LENGTH: 723
<212> TYPE: PRT
<213> ORGANISM: Artificial Sequence
<220> FEATURE:
<223> OTHER INFORMATION: Description of Artificial Sequence:
      KIKKTKK27AIATAA mutant of TCF-II

<400> SEQUENCE: 3

```
Met Trp Val Thr Lys Leu Leu Pro Ala Leu Leu Leu Gln His Val Leu
-31 -30                 -25                 -20

Leu His Leu Leu Leu Leu Pro Ile Ala Ile Pro Tyr Ala Glu Gly Gln
-15                 -10                 -5                  -1   1

Arg Lys Arg Arg Asn Thr Ile His Glu Phe Lys Lys Ser Ala Lys Thr
                5                   10                  15

Thr Leu Ile Lys Ile Asp Pro Ala Leu Ala Ile Ala Thr Ala Ala Val
            20                  25                  30

Asn Thr Ala Asp Gln Cys Ala Asn Arg Cys Thr Arg Asn Lys Gly Leu
    35                  40                  45

Pro Phe Thr Cys Lys Ala Phe Val Phe Asp Lys Ala Arg Lys Gln Cys
50                  55                  60                  65

Leu Trp Phe Pro Phe Asn Ser Met Ser Ser Gly Val Lys Lys Glu Phe
                70                  75                  80

Gly His Glu Phe Asp Leu Tyr Glu Asn Lys Asp Tyr Ile Arg Asn Cys
            85                  90                  95
```

```
Ile Ile Gly Lys Gly Arg Ser Tyr Lys Gly Thr Val Ser Ile Thr Lys
        100                 105                 110

Ser Gly Ile Lys Cys Gln Pro Trp Ser Ser Met Ile Pro His Glu His
    115                 120                 125

Ser Tyr Arg Gly Lys Asp Leu Gln Glu Asn Tyr Cys Arg Asn Pro Arg
130                 135                 140                 145

Gly Glu Glu Gly Gly Pro Trp Cys Phe Thr Ser Asn Pro Glu Val Arg
                150                 155                 160

Tyr Glu Val Cys Asp Ile Pro Gln Cys Ser Glu Val Glu Cys Met Thr
            165                 170                 175

Cys Asn Gly Glu Ser Tyr Arg Gly Leu Met Asp His Thr Glu Ser Gly
        180                 185                 190

Lys Ile Cys Gln Arg Trp Asp His Gln Thr Pro His Arg His Lys Phe
    195                 200                 205

Leu Pro Glu Arg Tyr Pro Asp Lys Gly Phe Asp Asp Asn Tyr Cys Arg
210                 215                 220                 225

Asn Pro Asp Gly Gln Pro Arg Pro Trp Cys Tyr Thr Leu Asp Pro His
                230                 235                 240

Thr Arg Trp Glu Tyr Cys Ala Ile Lys Thr Cys Ala Asp Asn Thr Met
            245                 250                 255

Asn Asp Thr Asp Val Pro Leu Glu Thr Thr Glu Cys Ile Gln Gly Gln
        260                 265                 270

Gly Glu Gly Tyr Arg Gly Thr Val Asn Thr Ile Trp Asn Gly Ile Pro
    275                 280                 285

Cys Gln Arg Trp Asp Ser Gln Tyr Pro His Glu His Asp Met Thr Pro
290                 295                 300                 305

Glu Asn Phe Lys Cys Lys Asp Leu Arg Glu Asn Tyr Cys Arg Asn Pro
                310                 315                 320

Asp Gly Ser Glu Ser Pro Trp Cys Phe Thr Thr Asp Pro Asn Ile Arg
            325                 330                 335

Val Gly Tyr Cys Ser Gln Ile Pro Asn Cys Asp Met Ser His Gly Gln
        340                 345                 350

Asp Cys Tyr Arg Gly Asn Gly Lys Asn Tyr Met Gly Asn Leu Ser Gln
    355                 360                 365

Thr Arg Ser Gly Leu Thr Cys Ser Met Trp Asp Lys Asn Met Glu Asp
370                 375                 380                 385

Leu His Arg His Ile Phe Trp Glu Pro Asp Ala Ser Lys Leu Asn Glu
                390                 395                 400

Asn Tyr Cys Arg Asn Pro Asp Asp Ala His Gly Pro Trp Cys Tyr
            405                 410                 415

Thr Gly Asn Pro Leu Ile Pro Trp Asp Tyr Cys Pro Ile Ser Arg Cys
        420                 425                 430

Glu Gly Asp Thr Thr Pro Thr Ile Val Asn Leu Asp His Pro Val Ile
    435                 440                 445

Ser Cys Ala Lys Thr Lys Gln Leu Arg Val Val Asn Gly Ile Pro Thr
450                 455                 460                 465

Arg Thr Asn Ile Gly Trp Met Val Ser Leu Arg Tyr Arg Asn Lys His
                470                 475                 480

Ile Cys Gly Gly Ser Leu Ile Lys Glu Ser Trp Val Leu Thr Ala Arg
            485                 490                 495

Gln Cys Phe Pro Ser Arg Asp Leu Lys Asp Tyr Glu Ala Trp Leu Gly
        500                 505                 510
```

-continued

```
Ile His Asp Val His Gly Arg Gly Asp Glu Lys Cys Lys Gln Val Leu
    515             520                 525
Asn Val Ser Gln Leu Val Tyr Gly Pro Glu Gly Ser Asp Leu Val Leu
530             535                 540                     545
Met Lys Leu Ala Arg Pro Ala Val Leu Asp Asp Phe Val Ser Thr Ile
                550                 555                 560
Asp Leu Pro Asn Tyr Gly Cys Thr Ile Pro Glu Lys Thr Ser Cys Ser
            565                 570                 575
Val Tyr Gly Trp Gly Tyr Thr Gly Leu Ile Asn Tyr Asp Gly Leu Leu
        580                 585                 590
Arg Val Ala His Leu Tyr Ile Met Gly Asn Glu Lys Cys Ser Gln His
    595                 600                 605
His Arg Gly Lys Val Thr Leu Asn Glu Ser Glu Ile Cys Ala Gly Ala
610             615                 620                     625
Glu Lys Ile Gly Ser Gly Pro Cys Glu Gly Asp Tyr Gly Gly Pro Leu
                630                 635                 640
Val Cys Glu Gln His Lys Met Arg Met Val Leu Gly Val Ile Val Pro
            645                 650                 655
Gly Arg Gly Cys Ala Ile Pro Asn Arg Pro Gly Ile Phe Val Arg Val
        660                 665                 670
Ala Tyr Tyr Ala Lys Trp Ile His Lys Ile Ile Leu Thr Tyr Lys Val
    675                 680                 685
Pro Gln Ser
690
```